United States Patent [19]

Yost

[11] 4,414,990

[45] Nov. 15, 1983

[54] FLUORIDATED DENTAL ARTICLES

[75] Inventor: Kevin G. Yost, Short Hills, N.J.

[73] Assignee: Johnson & Johnson Products, Inc., New Brunswick, N.J.

[21] Appl. No.: 364,716

[22] Filed: Apr. 2, 1982

[51] Int. Cl.³ ............................................. A61C 15/00
[52] U.S. Cl. ................................................... 132/91
[58] Field of Search ................ 132/89, 93, 91; 424/52

[56] References Cited

U.S. PATENT DOCUMENTS

| | | | |
|---|---|---|---|
| 2,381,142 | 8/1945 | Stonehill | 132/89 |
| 2,612,177 | 9/1952 | Footer | 132/93 |
| 2,700,636 | 1/1955 | Ashton | 132/89 |
| 3,830,246 | 8/1974 | Gillings | 132/89 |
| 3,838,702 | 10/1974 | Standish | 132/89 |
| 4,237,911 | 12/1980 | White | 132/89 |

Primary Examiner—Gregory E. McNeill
Attorney, Agent, or Firm—Steven P. Berman

[57] ABSTRACT

A fluoridated dental article for cleaning the interproximal surfaces of the teeth, such as dental floss or dental tape, comprising filaments coated with a wax coating that is in turn coated with a polymeric coating containing a fluoride salt.

15 Claims, No Drawings

FLUORIDATED DENTAL ARTICLES

BACKGROUND OF THE INVENTION

This invention relates to articles for cleaning the interproximal surfaces of the teeth and more particularly to dental floss and dental tape with fluoride incorporated therein and capable of delivering fluoride onto the tooth enamel.

It has been shown that tooth decay and dental disease can be attributed to bacterial action resulting from the formation of plaque about the teeth and/or the entrapment of food particles between the teeth and interstices therebetween. The removal of plaque and entrapped food particles reduces caries, reduces the tendency towards gingivitis, and reduces mouth odor as well as generally improving oral hygiene. Conventional brushing of the teeth has been found to be unsatisfactory to effect the removal of entrapped food particles from some crevices between the teeth and/or to effectively remove the plaque by which the bacteria adheres to the teeth. To supplement brushing, various materials have been used to clean the interproximal spaces and surfaces of the teeth, for example, dental floss and dental tape. It is to be understood that the use of the term "dental floss" hereinafter encompasses dental tape as well as any similar article.

The prior art recognizes fluorides as superior agents used in proper oral hygiene for the control of dental caries. Various dentifrices and rinses have been used as carriers to deliver fluoride to the tooth enamel surface. A dentifrice containing fluoride, even with proper brushing, cannot remove plaque or debris from within the interproximal spaces between teeth. Consequently brushing with such a dentifrice cannot be effective to cause significant attachment of fluoride ions to interproximal spaces. Similarly, rinses cannot remove plaque from interproximal areas and consequently are inadequate carriers to deliver fluoride ions to interproximal tooth enamel. Since a dental floss is able to penetrate the interproximal space between teeth, it does remove extraneous material therefrom, and, if impregnated with a source of fluoride soluble in the oral fluids, will deposit fluoride ions in oral fluids for incorporation of same into tooth enamel including incorporation into interproximal tooth enamel.

The prior art also explored the possibilities of incorporating a fluoride source into various waxes which then were coated on a dental floss. The use of wax-coated dental flosses are especially preferred by individuals having tightly contacting teeth since the wax coating renders lubrication to the floss and provides for easier manipulation of same between tightly contacting teeth. Notwithstanding the beneficial attributes, fluoride-containing, wax-coated dental flosses have a major disadvantage. Namely, the wax is impervious to, and not readily soluble in oral fluids and the length of time of the application is insufficient for the wax to release its charge of fluoride during the brief exposure to the oral fluids.

Accordingly, the present invention provides a wax-coated dental floss which is subsequently coated with a polymeric material that includes a source of fluoride. The polymeric material used must be capable of rapidly releasing fluoride in an aqueous environment.

The present invention also provides a dental floss having impregnated thereon biologically-active fluoride that is incorporable into human tooth enamel.

The invention further provides methods of manufacture of such dental floss.

SUMMARY OF THE INVENTION

The fluoride-containing dental floss of the present invention comprises a wax-coated dental floss overcoated with a film-forming composition comprising a polymer and a water-soluble fluoride salt. In use, oral fluids contact the polymeric coating and dissolve the fluoride salt therefrom. Also upon use, the polymeric coating splits or cracks, uncovering the wax-coated dental floss which then is able to clean the interproximal teeth area having both sufficient lubricity for easy insertion between teeth and tack for ease of handling. The dissolved fluoride salt remains behind at the specific site of application to allow incorporation of the fluoride into adjacent tooth enamel.

DETAILED DESCRIPTION OF THE INVENTION

The construction of the present invention comprises a dental floss substrate, an inner wax coating on the substrate, and an outer polymeric coating having incorporated therein a source of fluoride ions.

The Dental Floss Substrate

The dental floss substrate comprises a plurality of individual filaments of a substance suitable for use as a dental floss, including, for example, nylon 6 and 66, rayon, Dacron, acetate polymers, polypropylene and similar monofilament yarns as well as cotton, wool, and other staple yarns. The plurality of smaller fibers are combined together to form a yarn of larger size small enough to pass between closely contacting teeth. If desired, the yarn filaments can be colored utilizing any suitable dye such as FD&C Blue No. 1, FD&C Yellow No. 10, FD&C Green No. 3, FD&C Red No. 40, or mixtures of these or other similar dyes.

The preferred means of combining the fibers is to twist them together to form a floss product more resistant to shredding and filament separation than would otherwise be achieved. Dental floss can be made with little or no twist or it can be braided as in a dental tape. The twist can be from 0.0 to 6.0 turns per inch, with a preferred twist of 2.0 to 4.0 turns per inch.

The tensile strength of the finished floss should be between 5 and 25 pounds, although higher tensile strengths are acceptable. The preferred tensile strength is about 7 to 15 pounds. A finished yarn of less than 5 pounds will tend to break easily during use and would be unacceptable for a dental floss, and a finished yarn of more than 25 pounds tensile strength offers no advantages yet is less economical to manufacture. The yarn may be of 200 to 2000 denier, while the preferred dental floss is of 500 to 1600 denier for proper hand feel.

The Wax Coating

The preferred waxes for coating the dental floss substrate are those that are white or colorless and have a melting point of from 140° F. to 200° F. Suitable waxes include beeswax, parafin and microcrystalline waxes, polyethylene glycols such as those sold under the trademark "Carbowax" by Union Carbide Corp., New York, and the like as well as mixtures thereof. The wax comprises about 2% to 30% by weight of the dental floss, preferably about 10% to 25% by weight.

For added appeal, the wax portion of the dental floss could carry flavor oils spray dried into suitable water-soluble carriers. These flavors would then be included in the wax during the floss manufacture according to methods known to those familiar with the art. Upon use, the water present in the oral fluids will release the flavor.

The Polymeric Coating

The present invention utilizes polymeric materials as a carrier for the fluoride salts which are the source of fluoride ions. The polymeric coating must have good adhesion, clarity, toughness, and it must be non-toxic. Further, it is desirable that the polymeric material be a film former so that a uniform continuous coating can be achieved. It is further desired that the polymeric material be capable of hydration whereby the film so formed is water pervious allowing for rapid release of fluoride salt therefrom. Hydration in this context means the mechanism by which the polymeric material takes up and combines with water.

Good adhesion of the polymeric coating to the wax layer or coating of the floss is important to ensure composition integrity so that the fluoride salt incorporated into the polymeric coating remains adhered to the floss. Clarity of the coating is desirable to allow dyes applied to the yarn or the wax to be visible, and thus allow more aesthetic flexibility.

The polymeric coating should be sufficiently tough to resist abrasion of the floss to prevent cracking or flaking and resultant loss of the fluoride salt before placement of the dental floss in the oral cavity.

Specific polymeric coatings which are useful in the present invention include:
 a. alkyl monoesters of poly(methyl vinyl ether/maleic acid);
 b. polyvinyl pyrrolidones;
 c. acrylamide/acrylate/butylaminoethyl methacrylate polymers. Polymers of this type are sold by National Starch & Chemical Corporation under the trademark "Amphomer";
 d. vinyl acetate/crotonic acid/vinyl neodecanoate terpolymers. Terpolymers of this type are sold by National Starch & Chemical Corporation under the trademark "Resyn 28-2930";
 e. vinyl acetate/crotonic acid copolymers. Copolymers of this type are sold by the National Starch & Chemical Corporation under the trademark "Resyn 28-1310";
 f. terpolyamides comprised of the copolymerization products of three polyamide precursors, a dicarboxylic acid-diamine reaction product, a second but dissimilar dicarboxylic acid-diamine reaction product and a lactam. Terpolymers of this type are sold by Belding Chemical Industries as the BCI-600 series nylons;
 g. hydroxypropyl celluloses. Polymers of this type are sold by Hercules Incorporated under the trademark "Klucel".

The polymeric coating placed on the surface of the wax should comprise from about 1 to about 10 percent by weight of the final product. If it is less than about 1 percent of the product weight it will be ineffectual in keeping sufficient fluoride salt adhered to the dental floss. If it is more than about 10 percent of the product weight the coating adversely affects product aesthetics as a waxed dental floss.

THE SOURCE OF FLUORIDE IONS

The present invention utilizes fluoride salts as a source of fluoride ions.

The fluoride salt should be present in a concentration to provide 0.0002 to 2 milligrams of fluoride ion per centimeter of dental floss. If the fluoride salt level is less than 0.0002 milligrams fluoride ion per centimeter, insufficient fluoride is present for release during the flossing operation to allow sufficient fluoride uptake into tooth enamel and the dental floss could then be considered to be an effective source of fluoride. The floss should not carry above 2 milligrams fluoride per centimeter since no additional therapeutic effect can be expected from higher levels, and excessively high levels may be locally damaging to tissues. The preferred level of fluoride ion to be carried by the floss of this invention is about 0.02 to about 0.5 milligrams per centimeter.

The fluoride salts of choice may be sodium fluoride, stannous fluoride, titanium fluoride, sodium monofluorophosphate, aminefluoride, or any other suitable fluoride salt which is readily soluble in an aqueous environment and capable of delivering fluoride to tooth enamel. These salts should be composed of particles of 1 to 200 micrometers, preferably less than 50 micrometers. Small size of the particles allows uniform dispersion of the fluoride salt in the non-wax polymeric coating. The small size also allows ready dissolution of the fluoride salt during use in the oral cavity.

THE PROCESS OF MAKING FLOSS OF THE INVENTION

In accordance with one preferred production process, a selected filament or yarn, according to the above description, is passed through a bath of melted wax followed by passing the yarn through a chamber of refrigerated air to effect solidification of the wax. Alternatively, the coating may also be applied by passing the yarn through a bath of the wax in solution using a suitable solvent, such as methylene chloride. After coating, the solvent is flashed off using radiant heaters or high velocity hot air. If a dye and/or a flavor is to be included, the same is placed into the wax bath or solution and thus it is coated onto the filament along with the wax.

Once the wax layer has been applied to the dental floss substrate or filament, the polymeric coating and fluoride salt may be applied in a number of ways. The wax-coated yarn may pass through a solution of the polymeric coating in a volatile solvent and then, before the solvent has been flashed off, the fluoride salt is dusted onto the wet floss. Once coated, the floss is passed through an oven or drying chamber to flash off the solvent.

Alternatively, the solvent-wet floss, having been coated with the polymeric material, may be passed through the fluoride salt powder so that the tacky surface of the floss will pick up the salt and help it adhere to the surface. The floss is then passed through an oven or drying chamber to flash off the solvent.

Still another method of adding the fluoride to the floss is by spraying the wet floss with the powder as it is wound on the rewind supply spool just after the coating has occurred. This may cause some of the particles to be impregnated more firmly into the polymeric coating due to mechanical compression.

Still another method of impregnating the floss with a fluoride salt is the inclusion of the fluoride salt in the polymeric material solution tank. Since the fluoride particles tend to settle out in the tank, the slurry formed by the particles in the solution must be subjected to sufficient mixing to keep the particles in suspension. A homogeneous suspension is required to make the level of fluoride as uniformly distributed along the floss as possible. The floss is then passed through the slurry of coating and fluoride by means of guides or wheels. The floss thus coated with a layer of the wet slurry then is dried by standard means such as passing through an oven or drying chamber to flash off the solvent.

The floss of the present invention is capable of delivering fluoride to intact human enamel surfaces in levels comparable to those observed in the enamel surfaces of teeth treated with a fluoride dentifrice or fluoride rinse. Dental floss containing fluoride in accordance with this invention does not lose its fluoride charge upon aging at 50° C. for 12 weeks.

A dental floss in accordance with the present invention exhibits a desirable surface texture. It provides excellent cleaning to the interproximal surfaces of the teeth, while delivering an effective amount of fluoride to the teeth of the user to combat dental caries.

In addition to the embodiments described herein, other arrangements and variations within the scope and spirit of the invention will occur to those skilled in the art.

What is claimed is:

1. A fluoridated dental article comprising: a plurality of filaments of a substrate material formed into a thread having a diameter which permits insertion between the teeth; a wax coating substantially covering said thread and; a polymeric coating including a fluoride salt substantially covering said wax coating.

2. The fluoridated dental article of claim 1 wherein the substrate material is selected from the group consisting of nylon, rayon, Dacron, acetate, cotton, wool, polyester and polypropylene monofilaments.

3. The fluoridated dental article of claim 1 wherein said wax coating material is selected from the group consisting of beeswax, parafin, microcrystalline waxes, and polyethylene glycols, having a melting point of from about 140° to about 200° F.

4. The fluoridated dental article of claim 1 wherein said polymeric coating material is selected from the group consisting of:
   alkyl monoesters of poly(methyl vinyl ether/maleic acid);
   polyvinyl pyrrolidones;
   acrylamide/acrylate/butylaminoethyl methacrylate polymers;
   vinyl acetate/crotonic acid copolymers;
   vinyl acetate/crotonic acid/vinyl neodecanoate terpolymers;
   terpolyamides comprised of the copolymerization products of three polyamide precursors, a dicarboxylic acid-diamine reaction product, a second but dissimilar dicarboxylic acid-diamine reaction product and a lactam; and
   hydroxypropyl cellulose.

5. The fluoridated dental article of claim 1 wherein said fluoride salt impregnated into said polymeric coating is selected from the group consisting of sodium fluoride, stannous fluoride, sodium monofluorophosphate, ammonium fluoride, and titanium fluoride.

6. The fluoridated dental article of claim 1 wherein said wax coating comprises from about 2 to about 30 percent by weight of the final product.

7. The fluoridated dental article of claim 1 wherein said polymeric coating comprises from about 1 to about 10 percent by weight of the final product.

8. The fluoridated dental article of claim 1 wherein said fluoride ion content is from about 0.0002 to about 2 milligrams per centimeter in the final product.

9. The fluoridated dental article of claim 1 wherein said fluoride salt consists of particles from about 1 to about 100 micrometers.

10. The fluoridated dental article of claim 1 wherein said wax coating further comprises a dye.

11. The fluoridated dental article of claim 1 wherein said wax further comprises a spray-dried flavoring material.

12. The fluoridated dental article of claim 1 wherein the article is dental floss.

13. The fluoridated dental article of claim 1 wherein the article is dental tape.

14. The fluoridated dental article of claim 1 wherein the polymeric coating is impregnated with said fluoride salt.

15. The fluoridated dental article of claim 1 wherein said fluoride salt is surface coated onto said polymeric coating.

* * * * *